(12) United States Patent
De Bony et al.

(10) Patent No.: US 6,410,037 B1
(45) Date of Patent: Jun. 25, 2002

(54) ANTI-PRURITIC COMPOSITIONS

(75) Inventors: Raymond De Bony, Ecublens (CH); Eric Gooris, Neydens (FR)

(73) Assignee: Roche Consumer Health AG, Kaiseraugst (CH)

( * ) Notice: Subject to any disclaimer, the term of this patent is extended or adjusted under 35 U.S.C. 154(b) by 0 days.

(21) Appl. No.: 09/658,896

(22) Filed: Sep. 11, 2000

(30) Foreign Application Priority Data

Sep. 15, 1999 (EP) .......................................... 99118285

(51) Int. Cl.[7] .................................................. A61K 7/00
(52) U.S. Cl. ..................................................... 424/401
(58) Field of Search .................... 424/401; 514/801–865

(56) References Cited

U.S. PATENT DOCUMENTS

| | | | |
|---|---|---|---|
| 4,721,705 A | 1/1988 | Schreuder ..................... | 514/54 |
| 5,304,574 A | 4/1994 | Leung ......................... | 514/563 |
| 5,425,954 A * | 6/1995 | Thompson et al. ......... | 424/401 |
| 5,621,012 A | 4/1997 | Schönrock et al. ......... | 514/629 |
| 5,827,523 A | 10/1998 | Holland ..................... | 424/405 |

FOREIGN PATENT DOCUMENTS

| | | |
|---|---|---|
| DE | 19531893 | 3/1997 |
| DE | 19537509 | 4/1997 |
| DE | 19800982 | 7/1999 |
| EP | 0687467 | 12/1995 |
| WO | WO 9321899 | 11/1993 |

OTHER PUBLICATIONS

Abstract corresponding to DE 19537509.
Abstract corresponding to DE 19800982.
Abstract corresponding to DE 19531893.
Håkanson R., et al., Analytical Biochemistry, 47, pp. 356–370 (1972).
Paubert–Braquet M., et al., Thérapeutique, 95, Abstract pp. 1–4, (1992).

* cited by examiner

*Primary Examiner*—Jose' G. Dees
*Assistant Examiner*—Konata M. George
(74) *Attorney, Agent, or Firm*—George W. Johnston; Patricia Rocha-Tramaloni; Arthur D. Dawson

(57) ABSTRACT

The present invention relates to the use of pantothenic acid and/or its derivatives for treating dermatological disorders which involve mastocyte degranulation, such as atopic dermatitis, psoriasis, contact eczema, skin allergies, skin inflammation due to insect bites, skin allergies, senile pruritus, and to compositions comprising pantothenic acid and/or its derivatives, glycine and pharmaceutically and/or cosmetically acceptable additives which compositions are synergistic for the inhibition of mastocyte degranulation.

8 Claims, No Drawings

ANTI-PRURITIC COMPOSITIONS

BACKGROUND OF THE INVENTION

The present invention relates to compositions for blocking histamine release by mastocytes.

Degranulation of cutaneous mastocytes leads to the release of several mediators, including histamine. Histamine is responsible for different reactions, such as pruritus (itching). Histamine release can be amplified or inhibited by several substances. Histamine inhibitors can be used as active compounds in medicaments.

Glycine is an amino acid occurring naturally in most animal species. It inhibits histamine release by mastocytes. The effect of glycine on mastocyte degranulation is described, for instance, in M. Paubert-Braquet, G. Lefranqois, S. Picquot, D. Rod, *Thérapeutique*, 95, 1992, 2. A decrease in the amount of mediators released into the extra-cellular environment (e.g. histamine) has been observed, resulting from the inhibition of mastocyte degranulation.

The use of glycine for treating dermatological disorders which involve mastocyte degranulation is furthermore described in A. Siboulet, J M Bohbot, *Gyn. Obs.*, 1987, 166 by means of a study on pruriti in the genital area.

For a certain types of pruritus, such as allergic pruritus, the stimulus responsible for the degranulation of the mastocytes is a modification of the mastocyte membrane structure by a bipolar antigen. The antigen is fixed on two IgE which are nonspecifically attached to the cell membrane by their Fc extremities.

For many other types of pruritus, the mechanisms are still obscure. The stimuli maybe in fact of different nature, both chemical and physical, and may involve the presence of a neurotransmitter such as substance P. This substance, present naturally in the mammalian body, is capable of initiating mastocyte degranulation. Pruritus can be therefore treated in different ways, e.g. by blocking message transmission from the central nervous system, by blocking the stimulus and/or by inhibiting the degranulation process.

Pantothenic acid, which is also known as D(+) N-(2,4-dihydroxy-3,3-dimethylbutyryl)β-alanine, is a member of the B complex vitamins and is sometimes referred to as vitamin $B_5$.

Pantothenic acid plays a key role in cellular metabolism. After incorporation into coenzyme A (CoA), it participates in the synthesis of fatty acids, cholesterol and sterols. Through its participation in the Krebs cycle, coenzyme CoA is also instrumental in the generation of energy by the cells. Pantothenic acid is hence essential for epithelial regeneration and development in the event of skin damage when a high rate of lipid synthesis and cellular renewal is needed.

Dexpanthenol, the alcohol of pantothenic acid, is well absorbed by the skin. After penetration in the skin it is rapidly transformed into pantothenic acid. Dexpanthenol has therefore been used for many years in topical products such as ointments and creams. The clinical effectiveness of the topical application of dexpanthenol in promoting wound healing has been confirmed by several studies in cases of wounds, burns, cracked nipples, ulcers, and bedsores (e.g. P. Girard, A. Béraud, C. Goujon, A. Sirvent, J-L Foyatier, B. Alleaume, R. de Bony, *Les Nouvelles Dermatologiques*, 17, 1998, pp. 559–570).

SUMMARY OF THE INVENTION

It has been found that compositions containing pantothenic acid and/or its derivatives can be used for treating pruritic conditions. It has been observed that pantothenic acid and/or its derivatives inhibit mastocyte degranulation, thus diminishing the amount of mediators released into the extra-cellular environment. Pantothenic acid and/or its derivatives can be therefore used for all dermatological disorders which involve mastocyte degranulation, such as atopic dermatitis, psoriasis, contact eczema, skin allergies, skin inflammation due to insect bites, skin allergies, senile pruritus, etc.

It has also been found that the inhibition effect on mastocyte degranulation is strongly increased if pantothenic acid and/or its derivatives are combined with glycine. A synergistic effect in the inhibition by the mixture in comparison with the single compounds is therefore observed.

Therefore, this invention is directed to a method of treating a dermatological disorder related to mastocyte degranulation (such as atopic dermatitis, psoriasis, contact eczema, skin allergies, skin inflammation due to insect bites, skin allergies, senile pruritus) which comprises administering pantothenic acid or a derivative thereof in an amount effective to alleviate the dermatological disorder.

This invention is also directed to compositions comprising pantothenic acid or a derivative thereof and glycine. These compositions are synergistic in their effects on dermatological disorders. Methods of treating dermatological disorders with these compositions are another part of this invention. The synergistic effect obtained by mixing the above compounds together leads to several important advantages. For the same effect, it is possible to reduce the concentrations of the active compounds, thus decreasing the risk of intolerance for the patients. A lower concentration of the active compounds lead also to lower manufacturing costs and, therefore, to lower selling prices of the compositions. With the same therapeutic effect, the compositions according to the present invention are therefore more tolerable and more competitive than the conventional ones.

In preferred methods and compositions of the present invention, pantothenic acid and/or its derivatives are used in an amount from 0.1% to 10%, inclusive, in other words varying between 0.1 and 10%, of total weight of the pharmaceutical and/or cosmetic composition and, preferably, in an amount from 2% to 5% inclusive, in other words varying between 2 and 5%, of the total weight. All ranges given herein are considered inclusive of each end of the range.

DETAILED DESCRIPTION OF THE INVENTION

This invention is directed to a method of treating a dermatological disorder related to mastocyte degranulation (such as atopic dermatitis, psoriasis, contact eczema, skin allergies, skin inflammation due to insect bites, skin allergies, senile pruritus) which comprises administering pantothenic acid or a derivative thereof in an amount effective to alleviate the dermatological disorder. Preferably the effective amount of pantothenic acid or a derivative thereof is from 0.1% to 10% (more preferably from 2% to 5%) of the total weight of the composition in which it is administered.

This invention is also directed to a method of treating a dermatological disorder related to mastocyte degranulation (such as atopic dermatitis, psoriasis, contact eczema, skin allergies, skin inflammation due to insect bites, skin allergies, senile pruritus) which comprises administering pantothenic acid or a derivative thereof and glycine in an amount effective to alleviate the dermatological disorder. Preferably the ratio of pantothenic acid to glycine varies from 0.13 to 13.3 wt/wt. in the composition in which they are administered. In one embodiment, the effective amounts of pantothenic acid or a derivative thereof and the glycine are each from 0.1% and 10% (preferably from 2% and 5%) of the total weight of the composition in which they are administered. In this embodiment, the ratio of the two components may be from 0.13 to 13.3 as above.

By "alleviate" is meant remove or reduce symptoms in the humans or animals to which the compositions of this invention are administered. For example a perceived reduction in itching constitutes alleviation, as does reduction in rash area, or fading of color. Reduction in histamine production as measured by any conventional assay is another example of alleviation.

This invention is further directed to a pharmaceutical composition comprising pantothenic acid or a derivative thereof, glycine, and a pharmaceutically acceptable carrier, and a composition for topical application comprising pantothenic acid or a derivative thereof, glycine, and an acceptable carrier for topical application. In each composition, it is preferred that the ratio of pantothenic acid or a pantothenic acid derivative to glycine varies from 0.13 to 13.3 wt/wt, inclusive, in other words the ratio between pantothenic acid and/or its derivatives and glycine varies between 0.13 and 13.3wt/wt. It is also preferred that in the above compositions (including the compositions with the specific ratio of 0.13 to 13.3) the pantothenic acid or a derivative thereof and the glycine are each present in an amount varying from 0.1% and 10% of the total weight of the composition, and preferably from 2% and 5% of the total weight of the composition.

Any pharmaceutically and/or cosmetically acceptable derivative of pantothenic acid can be used in the compositions of the present invention. Examples include alcohols, aldehydes, alcohol esters, acid esters and the like. The preferred derivative of pantothenic acid is pantothenyl alcohol (panthenol), particularly the D(+) form of pantothenyl alcohol which is more commonly known as dexpanthenol. As preferred alcohol ester, pantothenyl triacetate can be chosen.

The present invention relates also to the use of pantothenic acid and/or its derivatives for the manufacture of topically applicable pharmaceutical and/or cosmetic compositions for treating dermatological disorders which involve mastocyte degranulation, such as atopic dermatitis, psoriasis, contact eczema, skin allergies, skin inflammation due to insect bites, skin allergies, senile pruritus, etc.

A further aspect of the present invention is related to the use of a mixture of pantothenic acid and/or its derivatives and glycine for the manufacture of a medicament for treating dermatological disorders which involve mastocyte degranulation, such as atopic dermatitis, psoriasis, contact eczema, skin allergies, skin inflammation due to insect bites, skin allergies, senile pruritus, etc. Preferably, pantothenic acid and/or its derivatives and glycine are present in the mixture in a ratio varying between 0.13 and 13.3 wt/wt as described above.

Both pantothenic acid and/or its derivatives, and compositions of pantothenic acid and/or its derivatives and glycine, can be administered orally or be applied topically to the skin of a human or animal at the site of the disorder.

Pantothenic acid and/or its derivatives and the mixtures of pantothenic acid and/or its derivatives and glycine can be administered orally in the form of tablets, coated tablets, dragees, hard and soft gelatine capsules, solutions, emulsions or suspensions. The active compounds can be processed with pharmaceutically inert, inorganic or organic excipients, such as lactose, cornstarch or derivatives thereof, talc, stearic acid or its salts. Suitable excipients for soft gelatine capsules are e.g. vegetable oils, waxes, fats, semi-solid and liquid polyols etc. Suitable excipients for the manufacture of solutions and syrups are e.g. water, polyols, saccharose, invert sugar, glucose etc.

Moreover, the pharmaceutical and/or cosmetic compositions can contain preservatives, solubilizers, stabilizers, wetting agents, emulsifiers, sweeteners, colorants, flavorants, salts for varying the osmotic pressure, buffers, masking agents or antioxidants. They can also contain still other active substances, such as further vitamins, minerals, sun filters, phytotherapeutic extracts, or any other active substances.

For topical administration, the above active compounds are conveniently used in the form of pharmaceutical and/or cosmetic preparations or compositions which further contain an acceptable carrier material. Topical dosage forms provided by the invention generally contain 0.1 to 10 weight percent (inclusive), of active compound based on the total weight of the dosage form. However, higher or lower concentrations can also be present depending on the dosage form which is used. The topical preparations of the present invention can be applied in an amount and under a time schedule varying with the needs of the patient.

The term "topical" as used in the present specification relates to the use of the above active compounds, which are processed with a suitable carrier material and which is applied to the skin or mucous membrane, so that it can display local activity. Accordingly, the topical forms embrace pharmaceutical and/or cosmetic dosage forms which are suitable for external use, so that a direct contact with the skin results. The topical dosage forms embrace gels, creams, lotions, salves, powders, aerosols and other conventional forms which are suitable for the direct application of products on the skin or mucous membrane. These dosage forms can be manufactured by mixing the above compounds with known carrier materials which are suitable for topical use.

Salves and creams contain oily, absorbent, water-soluble and/or emulsifying carrier materials such as vaseline, paraffin oil, propylene glycol, cetylalcohol, glycerine monostearate, alkyl-branched fatty acids and the like.

Lotions are liquid preparations and can vary from simple solutions to aqueous or aqueous/alcoholic preparations which contain the substances in finely divided form. The preparations contain suspended or dispersing substances such as, for example, sodium carboxymethylcellulose which suspend or disperse the active substance in a carrier prepared from water, alcohol, glycerine and the like.

Gels are semi-solid preparations which are obtained by gelling a solution or suspension of the active substance in a carrier material. The carrier materials, which can be hydrophilic or hydrophobic, are gelled using a gelling agent in form of polymers of biological, natural or synthetic origin.

Aerosols are solutions or suspensions of the active substance in a carrier material which are applied using spray generators. Usually used carriers are, for example, trichloromonofluoromethane, trichlorodifluoromethane, volatile silicones, nitrogen, etc. Sprays are solutions suspensions or powders of the active substance in a carrier material which are applied using mechanical pumps.

The compositions according to the present invention are used by applying an amount of the active compounds sufficient to provide a therapeutic and/or cosmetic effect to the skin to be treated. This application can be effected in the usual manner by rubbing, spraying or by a plaster. The topical compositions are usually applied in an amount to provide from 0.1 to 5 mg (inclusive) of active ingredient per $cm^2$ of the skin per day.

It is also an object of the present invention to provide a process for preparing the above pharmaceutical and/or cosmetic compositions, comprising mixing pantothenic acid and/or its derivatives with glycine.

The following examples further illustrate the invention. Glycine and calcium pantothenate were provided by ROCHE and they were conserved at 4° C. until their use. Substance P was provided by SIGMA and the analytic reagents were provided by SIGMA, MERCK, BDH, ALDRICH, FLUKA or CARLO ERBA unless otherwise specified.

Test were carried out on peritoneal mastocytes of rat stimulated by the substance P (10 μM), or on human skin tissue.

Peritoneal Mastocytes of Rat

Peritoneal mastocytes of rat were incubated with the test products and the substance P for 2 minutes at 37° C. in the following medium: sodium phosphate buffer 4 mM; potassium phosphate buffer 2.7 mM; NaCl 0.145 M; KCl 2.7 mM; $CaCl_2$ 0.9 mM; BSA (bovine serum albumin 0.175% (w/v). At the end of the incubation, histamine released by the mastocytes was quantified by spectrofluorimetry with ortho-phthalaldehyde (OPT) (R. Hakanson, A. I. Ronnberg and K. Sjolund, *Analy. Biochem.*, 47,1972, pp. 356–370). The measurements were carried out by means of a multiplate spectrofluorimeter (Cytofluor 2350, MILLIPORE). Data groups (control and treated groups) were compared using a one-way analysis of variance (ANOVA 1, p<0.05), following by a Dunnett' test (p<0.05).

Glycine and calcium pantothenate were tested in combination as follow:

TABLE 1

Test combinations.

| Ca-pantothenate (μg/ml) | Glycine (μg/ml) | | | | |
|---|---|---|---|---|---|
| 10 | 7.50 | 18.75 | 37.50 | 56.25 | 75.00 |
| 25 | 7.50 | 18.75 | 37.50 | 56.25 | 75.00 |
| 50 | 7.50 | 18.75 | 37.50 | 56.25 | 75.00 |
| 75 | 7.50 | 18.75 | 37.50 | 56.25 | 75.00 |
| 100 | 7.50 | 18.75 | 37.50 | 56.25 | 75.00 |

The inhibition of the histamine release for different compositions tested on peritoneal mastocytes of rat is depicted in Table 2.

TABLE 2

Inhibition in Peritoneal mastocytes of rat.

| Example | Ca-pantothenate (μg/ml) | Glycine (μg/ml) | Inhibition[1] |
|---|---|---|---|
| 1 | 0 | 0 | 100 |
| 2 | 10 | 0 | 100 |
| 3 | 0 | 7.5 | 100 |
| 4 | 10 | 7.5 | 48 |
| 5 | 10 | 18.75 | 44 |
| 6 | 10 | 37.50 | 1 |
| 7 | 10 | 56.25 | 21 |
| 8 | 10 | 75.00 | −11 |
| 9 | 25 | 7.5 | 65 |

TABLE 2-continued

Inhibition in Peritoneal mastocytes of rat.

| Example | Ca-pantothenate (μg/ml) | Glycine (μg/ml) | Inhibition[1] |
|---|---|---|---|
| 10 | 25 | 18.75 | 49 |
| 11 | 25 | 37.50 | −14 |
| 12 | 25 | 75.00 | −8 |
| 13 | 50 | 7.5 | 54 |
| 14 | 50 | 18.75 | 48 |
| 15 | 50 | 37.50 | 31 |
| 16 | 50 | 56.25 | 13 |
| 17 | 50 | 75.00 | 9 |
| 18 | 75 | 7.5 | 63 |
| 19 | 75 | 18.75 | 49 |
| 20 | 75 | 37.50 | 35 |
| 21 | 75 | 75.00 | 14 |
| 22 | 100 | 7.5 | 59 |
| 23 | 100 | 18.75 | 41 |
| 24 | 100 | 37.50 | 29 |
| 25 | 100 | 56.25 | 10 |
| 26 | 100 | 75.00 | 12 |

[1]amount of histamine released by the mastocytes. Value 100 refers to the amount of histamine released by the substance P in absence of Ca-pantothenate and/or glycine, while value 0 refers to the release of histamine in normal conditions, i.e. in the absence of histamine release inducing agents. Negative values represent histamine concentrations which are lower than those observable at normal conditions.

value 0 refers to the release of histamine in normal conditions, i.e. in the absence of histamine release inducing agents. Negative values represent histamine concentrations which are lower than those observable at normal conditions.

The data in table 2 show that mixtures of Ca-panthothenate and glycine in different concentrations strongly inhibit the histamine release.

It has been furthermore shown that a synergistic effect resulting from combining Ca-panthothenate and glycine occurs. Concentrations of 10 μg/ml of Ca-panthothenate and 7.5 μg/ml of glycine, if taken separately, do not act as inhibitors while, if taken together, they strongly block the histamine release (see examples 2, 3 and 4 in table 2). This synergistic effect enables a large decrease in the concentrations of the active compounds in the medicaments, thus improving their tolerance and decreasing their manufacture costs.

Human Skin Tissue

The skin tissue assay system was prepared from normal adult skin collected after abdominal plastic surgery. The subject was a 68 years old woman (subject M1085). The skin tissue specimen was rinsed in Krebs bicarbonate solution consisting of: NaCl 118 mM; KCl 5.4 mM; $NaH_2PO_4$ 1 mM; $MgSO_4$ 1.2 mM, $CaCl_2$ 1.9 mM; $NaHCO_3$ 25 mM and D-glucose 11.1 mM. Skin discs of about 8 mm of diameter were performed. Skin discs were cultured in RPMI 1640 medium supplemented with penicillin (100 UI/ml), streptomycin (110 μg/ml) and 2 mM glutamine. Skin discs were maintained at 37° C. in a humidified incubator under a 5% $Co_2$/95% air atmosphere. Test products were incubated with the human skin discs and 100 μM of substance P for 2 hours at 37° C.

At the end of the incubation, histamine released by the human skin discs was quantified by ELISA (IMMUNOTECH). The results were expressed as pmoles of histamine released per gram of skin. Data groups (control and treated groups) were compared using a one-way analysis of variance (ANOVA 1, p<0.05), following by a Dunnett's test (p<0.05).

The inhibition of the histamine release for different compositions tested on human skin is depicted in Table 3.

| Ca-pantothenate (μg/ml) | Glycine (μg/ml) | Inhibition[1] |
|---|---|---|
| 25 | 0 | 84 |
| 50 | 0 | 84 |
| 100 | 0 | 80 |
| 100 | 75 | 60 |

[1]amount of histamine released by the mastocytes. Value 100 refers to the amount of histamine released by the substance P in absence of Ca-pantothenate and/or glycine, while value 0 refers to the release of histamine in normal conditions, i.e. in the absence of histamine release inducing agents. Negative values represent histamine concentrations which are lower than those observable at normal conditions.

The data of table 3 show that Ca-pantothenate acts as inhibitor of the histamine release already at a concentration of 25 μg/ml and that the addition of glycine further improves such inhibition.

EXAMPLE 1

Ointment Containing Dexpanthenol and Glycine

The topical composition is prepared by combining the following available components utilizing conventional techniques:

| | |
|---|---|
| Dexpanthenol | 5 wt % |
| Glycine | 3 wt % |
| Cetyl alcohol | 1.5 wt % |
| Stearyl alcohol | 1.5 wt % |
| Lanolin alcohol | 1.5 wt % |
| Glyceryl oleate | 1.5 wt % |
| Almond oil | 4.0 wt % |
| White wax | 5.5 wt % |
| Wool fat | 25 wt % |
| Vaseline white | 10 wt % |
| Paraffin liquid | 15 wt % |
| Ozokerite | 1.5 wt % |
| Water | balance |

EXAMPLE 2

Lotion Containing Dexpanthenol and Glycine

The topical composition is prepared by combining the following available components utilizing conventional techniques:

| | |
|---|---|
| Dexpanthenol | 2 wt % |
| Glycine | 0.2 wt % |
| PEG-6-stearat | 4 wt % |
| Dimethicone | 1.5 wt % |
| Paraffin liquid | 4 wt % |
| Pantolactone | 0.2 wt % |
| EDTA | 0.2 wt % |
| Phenoxyethanol | 0.7 wt % |
| Perfume | 0.5 wt % |
| Water | balance |

EXAMPLE 3

Capsules Containing Dexpanthenol and Glycine

The oral composition is prepared by combining the following available components utilizing conventional mixing techniques:

| | |
|---|---|
| Dexpanthenol | 100 mg/capsule |
| Glycine | 50 mg/capsule |
| Polyethylen glycol | 1.5 mg/capsule |
| Starch | 50 mg/capsule |
| Magnesium stearate, | 1.5 mg/capsule |
| Lactose | 100 mg/capsule |
| Talc | 1.5 mg/capsule |

What is claimed is:

1. A topical pharmaceutical composition comprising pantothenic acid or a derivative thereof and glycine in a pharmaceutically acceptable carrier, wherein a synergistic weight/weight ratio of the pantothenic acid, or pantothenic acid derivative, to the glycine is between about 0.13 and about 13.3 and wherein the pantothenic acid or pantothenic acid derivative and the glycine are each present in the composition in an amount between about 2% and 5% by weight.

2. The topical pharmaceutical composition of claim 1 wherein said pantothenic acid and said derivatives of pantothenic acid are selected from the group consisting of alcohols, aldehydes, alcohol esters and acid esters, the racemic or optical isomers of pantothenic acid or alcohol, aldehyde, alcohol esters and acid esters of pantothenic acid and combinations thereof.

3. The topical pharmaceutical composition of claim 2 wherein said pantothenic acid derivatives are selected from the group consisting of pantothenyl alcohol, D(+) pantothenyl alcohol and pantothenyl triacetate or combinations thereof.

4. A method of treating a dermatological condition related to mastocyte degranulation in a patient in need of such treatment comprising applying a sufficient quantity of a pharmaceutical composition comprising pantothenic acid or a pantothenic acid derivative and glycine in a pharmaceutically acceptable topical carrier to the skin of the patient, the pharmaceutical composition having a synergistic weight/weight ratio of the pantothenic acid or the pantothenic acid derivative to the glycine between about 0.13 and about 13.3, and wherein an amount of each of the pantothenic acid or pantothenic acid derivative and the glycine in the pharmaceutical composition is between about 2% to about 5% by weight of the composition.

5. The method of claim 4 wherein the quantity of the pharmaceutical composition applied to the skin delivers between about 0.1 mg to about 0.5 mg of the pantothenic acid or pantothenic acid derivative and the glycine per square centimeter of skin.

6. A method of reducing the release of histamine from mastocytes comprising administering a sufficient quantity of a pharmaceutical composition comprising pantothenic acid or a pantothenic acid derivative and glycine in a pharmaceutically acceptable carrier to a patient, the pharmaceutical composition having a synergistic weight/weight ratio of pantothenic acid or pantothenic acid derivative to glycine between about 0.13 and about 13.3, and wherein the amount of each of the pantothenic acid or pantothenic acid derivative and the glycine in the pharmaceutically acceptable carrier is between about 2% to about 5%.

7. The topical pharmaceutical composition of claim 3 wherein said derivative of pantothenic acid is D(+) pantothenyl alcohol.

8. The topical pharmaceutical composition of claim 3 wherein said derivative of pantothenic acid is pantothenyl triacetate.

* * * * *